United States Patent
Watschke et al.

(10) Patent No.: US 11,020,021 B2
(45) Date of Patent: Jun. 1, 2021

(54) BLADDER MAPPING

(71) Applicant: Boston Scientific Scimed, Inc., Maple Grove, MN (US)

(72) Inventors: Brian Watschke, Minneapolis, MN (US); Timothy Harrah, Cambridge, MA (US); Avshalom Shenhav, Haifa (IL); Yosi Hazan, Haifa (IL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/883,401

(22) Filed: Jan. 30, 2018

(65) Prior Publication Data

US 2018/0220938 A1    Aug. 9, 2018

Related U.S. Application Data

(60) Provisional application No. 62/455,320, filed on Feb. 6, 2017.

(51) Int. Cl.
| | |
|---|---|
| *G06K 9/00* | (2006.01) |
| *A61B 5/11* | (2006.01) |
| *A61B 1/307* | (2006.01) |
| *A61B 5/20* | (2006.01) |
| *A61B 1/00* | (2006.01) |
| *A61B 18/00* | (2006.01) |
| *A61B 5/392* | (2021.01) |

(52) U.S. Cl.
CPC ........ *A61B 5/1107* (2013.01); *A61B 1/00009* (2013.01); *A61B 1/307* (2013.01); *A61B 5/205* (2013.01); *A61B 5/392* (2021.01); *A61B 2018/00517* (2013.01)

(58) Field of Classification Search
None
See application file for complete search history.

(56) References Cited

U.S. PATENT DOCUMENTS

| | | |
|---|---|---|
| 8,600,135 B2 | 12/2013 | Patriarche et al. |
| 2006/0127880 A1 | 6/2006 | Harris et al. |

(Continued)

FOREIGN PATENT DOCUMENTS

| | | |
|---|---|---|
| WO | WO 96/09000 A1 | 3/1996 |
| WO | WO 2007/105213 A2 | 9/2007 |

OTHER PUBLICATIONS

Maurice "Endoscopic Gold Fiducial Marker Placement into the Bladder Wall to Optimize Radiotherapy Targeting for Bladder-Preserving Management of Muscle-Invasive Bladder Cancer: Feasibility and Initial Outcomes", PLoS ONE 9(3), 2014, pp. 1-10. (Year: 2014).*

(Continued)

*Primary Examiner* — Wei Wen Yang
(74) *Attorney, Agent, or Firm* — Bookoff McAndrews, PLLC (57) ABSTRACT

Aspects of bladder mapping are described herein. According to one aspect, an exemplary method comprises: generating, with an imaging element, a video feed depicting a bladder wall; establishing, with a processor, markers on the bladder wall in the video feed; tracking, with the processor, relative movements between the markers; and/or identifying, with the processor, a location of a contraction of the bladder wall based on the relative movements. Associated devices and systems also are described.

20 Claims, 10 Drawing Sheets

(56) References Cited

U.S. PATENT DOCUMENTS

| | | |
|---|---|---|
| 2013/0018281 A1 | 1/2013 | Nagale et al. |
| 2015/0320296 A1 | 11/2015 | Morita |
| 2016/0120598 A1 | 5/2016 | Brink et al. |
| 2016/0331450 A1 | 11/2016 | Ben-Ezra et al. |
| 2017/0046833 A1* | 2/2017 | Lurie ............... G06T 19/20 |
| 2017/0065821 A1 | 3/2017 | Brink et al. |

OTHER PUBLICATIONS

Southern "Elevated steady-state bladder preload activates myosin phosphorylation: detrusor smooth muscle is a preload tension sensor", Am J Physiol 303: F1517-F1526, 2012. (Year: 2012).*
International Search Report and Written Opinion in PCT/US2018/015876, dated Apr. 26, 2018 (15 pages).

* cited by examiner

STEP 120: GENERATING, WITH AN IMAGING ELEMENT, A VIDEO FEED OF A BLADDER WALL.

STEP 140: ESTABLISHING, WITH A PROCESSOR, MARKERS ON THE BLADDER WALL IN THE VIDEO FEED.

STEP 160: TRACKING, WITH THE PROCESSOR, RELATIVE MOVEMENTS BETWEEN THE MARKERS.

STEP 180: IDENTIFYING, WITH THE PROCESSOR, A LOCATION OF A CONTRACTION OF THE BLADDER WALL BASED ON THE RELATIVE MOVEMENTS.

BLADDER MAPPING

CROSS-REFERENCE TO RELATED APPLICATIONS

This patent application claims the benefit of priority under 35 U.S.C. § 119 to U.S. Provisional Patent Application No. 62/455,320, filed Feb. 6, 2017, which is herein incorporated by reference in its entirety.

TECHNICAL FIELD

Aspects of the present disclosure generally relate to medical devices and procedures. Particular aspects relate to bladder mapping.

BACKGROUND

A variety of disorders may challenge healthy bladder functions, such as disorders originating from age, injury, or illness. Some disorders cause improper communications between the nervous system and the bladder muscles. For example, some disorders disrupt communications between nerves and muscles of the bladder, resulting in spontaneous contractions or movements at locations on the bladder wall. Identifying the location of each contraction may aid in treatment. Because the contractions produce measurable electrical activity, the location of some contractions may be identified by placing an electrode in physical contact with the bladder wall, and measuring electrical activity with the electrode.

Accurately identifying the location of contractions can be costly and time-consuming to obtain with electrode-based methods. For example, the contractions can occur at any location on the bladder wall, meaning that the location of an electrode may not always coincide with the location of a contraction, requiring additional operating time for configuration. As a further example, placing electrodes in physical contact with the bladder wall may induce artificial muscle contractions, requiring the user to determine whether an electrical measurement is indicative of a spontaneous muscle contraction, or merely an artifact of physical contact with the bladder wall. This determination also may take additional operating time.

Aspects of bladder mapping described herein may address these issues and/or other deficiencies of the prior art.

SUMMARY

One aspect is a method. The method may comprise: generating, with an imaging element, a video feed depicting a bladder wall; establishing, with a processor, markers on the bladder wall in the video feed; tracking, with the processor, relative movements between the markers; and identifying, with the processor, a location of a contraction of the bladder wall based on the relative movements.

According to this aspect, an exemplary method may further comprise positioning the imaging element adjacent the bladder wall, such as adjacent to an exterior or interior surface of the bladder wall. Establishing the markers may comprise: locating in a first frame of the video feed, with the processor, a natural feature of the bladder wall; assigning, with the processor, a first marker to the natural feature in the first frame; locating in a second frame of the video feed, with the processor, the natural feature on the bladder wall; and assigning, with the processor, a second marker to the natural feature in the second frame. In some aspects, establishing the markers may comprise generating, with the processor, a first binary image of the first frame and a second binary image of the second frame; each of the first and second binary images may include data points defining a synthetic geometry of the natural feature; and the locating and assigning steps may further comprise: locating in the first and second binary images, with the processor, the location of the natural feature by generating a correlation between a reference pattern and data points from the synthetic geometry; and assigning, with the processor, the first and second markers to the data points based on the correlation. The reference pattern may, for example, include an X or Y shape corresponding with a blood vessel bifurcation.

Tracking the relative movements may comprise: establishing, with the processor, a tracking area of the bladder wall in the first and second frames that includes the first and second markers; and analyzing, with the processor, relative movements between the first and second markers in the tracking area to determine one or more movement vectors; and identifying the location of the contraction may comprise analyzing the one or more movement vectors.

Identifying the location of the contraction may comprise: locating, with the processor, a center of movement for the one or more movement vectors in the tracking area; and determining, with the processor, a magnitude of each movement vector and a distance from the center of movement for each movement vector. In some aspects, identifying the location may comprise: comparing, with the processor, the magnitude and distance of each movement vector with known movement characteristics to determine whether the relative movements were caused by the contraction or a movement of the imaging element. The method may further comprise: generating, with the processor, a ratio of the magnitude of each movement vector to the distance from the center of movement for each movement vector; qualifying, with the processor, the contraction when the ratio is parabolic; and disqualifying, with the processor, the contraction when the ratio is linear.

The method may further comprise: determining from the relative movements, with the processor, characteristics of the contraction including at least one of a contraction strength, a contraction frequency, a contraction profile, a contraction duration, and a contraction density; and diagnosing, with the processor, a condition of the bladder wall based on the characteristics of the contraction. The method also may comprise monitoring, with a sensor, characteristics of the bladder wall including at least one of a fluid pressure applied to the bladder wall and a volume of fluid retained by the bladder wall; generating, with the processor, a correlation between the characteristics of the contraction and the characteristics of the bladder wall; and diagnosing, with the processor, the condition of the bladder wall based on at least one of the characteristics of the contraction, the characteristics of the bladder wall, and the correlation therebetween.

The method may also comprise selecting, with the processor, a treatment for application to the location of the contraction; and/or applying the treatment. The treatment may include a wave energy, such as light or sound.

Another aspect is a method. This method may comprise: locating in frames of a video feed, with a processor, a natural feature of a bladder wall depicted in the video feed; assigning, with the processor, markers to the natural feature in each frame of the video feed; establishing, with the processor, a tracking area of the bladder wall in video feed that includes the first and second markers; analyzing, with the processor, relative movements of the markers in the tracking area to determine one or more movement vectors; locating, with the processor, a center of movement for the one or more movement vectors; and qualifying, with the processor, a movement of the bladder wall as a contraction based a ratio between the magnitude of each movement vector and a distance from the center of movement for each movement vector. For example, the natural feature may include a blood vessel bifurcation.

A method according to this aspect may further comprise: generating, with the processor, a binary image of each frame in the video feed, each binary image including data points defining a synthetic geometry of the bladder wall; locating in each binary image, with the processor, the natural feature by generating a correlation between a reference pattern and data points from the synthetic geometry; and assigning, with the processor, the first and second markers to the data points based on the correlation. This method also may comprise: identifying, with the processor, the location of each qualified contraction based on the one or more movement vectors; outputting, with the processor, the video feed to a display device; and overlaying onto the video feed, with the processor, the location of each qualified contraction, and/or characteristics of each qualified contraction including, for example, at least one of a contraction strength, a contraction frequency, a contraction profile, a contraction duration, and a contraction density. The method may further comprise: monitoring, with one or more sensors, characteristics of the bladder wall including at least one of a fluid pressure applied to the bladder wall and a fluid volume retained by the bladder wall; generating, with the processor, a correlation between the characteristics of each qualified contraction and the characteristics of the bladder wall; and diagnosing, with the processor, the condition of the bladder wall based on at least one of the characteristics of the contraction, the characteristics of the bladder, and the correlation therebetween.

Yet another aspect is a method. This additional method may comprise: selecting from a video feed, with a processor, a first frame depicted a bladder wall, and a second frame depicting the bladder wall; generating, with the processor, a first binary image of the first frame and a second binary image of the second frame; locating in the first and second binary images, with the processor, one or more blood vessel bifurcations of the bladder wall; assigning, with the processor, a first maker relative to the one or more blood vessel bifurcations in the first frame, and a second maker relative to the one or more blood vessel bifurcations in the second frame; calculating, with the processor, relative movements between the first and second markers; and identifying, with the processor, a location of one or more contractions of the bladder wall based on the relative movements.

A method according to this aspect may comprise receiving the video feed, at the processor, from an imaging element positioned adjacent the bladder wall. The method may further comprise: determining from the relative movements, with the processor, characteristics of the contraction; monitoring, with a sensor, characteristics of the bladder wall including at least one of a fluid pressure applied to the bladder wall and a volume of fluid retained by the bladder wall; and generating, with the processor, a correlation between the characteristics of the contraction and the characteristics of the bladder wall. For example, the method may comprise: diagnosing, with the processor, a condition of the bladder wall based on at least one of the characteristics of the contraction, the characteristics of the bladder wall, and the correlation therebetween.

It is understood that both the foregoing summary and the following detailed descriptions are exemplary and explanatory only, neither being restrictive of the inventions claimed below.

BRIEF DESCRIPTION OF THE DRAWINGS

The accompanying drawings are incorporated in and constitute a part of this specification. These drawings illustrate aspects of the present disclosure that, together with the written descriptions herein, serve to explain this disclosure. Each drawing depicts one or more exemplary aspects according to this disclosure, as follows.

DETAILED DESCRIPTION

Aspects of the present disclosure are now described with reference to exemplary devices, methods, and systems for bladder mapping. Some aspects are described with reference to medical procedures where an imaging element is located adjacent a wall of an organ, such as the wall of a bladder. References to a particular type of procedure, such as a medical procedure; imaging element, such as a camera; organ, such as a bladder; and/or organ wall, such as a bladder or muscle wall, are provided for convenience and not intended to limit this disclosure. Accordingly, the concepts described herein may be utilized for any analogous mapping methods—medical or otherwise.

Numerous axes are described herein. Each axis may be transverse or even perpendicular with the next to establish a Cartesian coordinate system with an origin point O. One axis may extend along a longitudinal axis of an object. The directional terms "proximal" and "distal," and their respective initials "P" and "D," may be utilized along with terms such as "parallel" and "transverse" to describe relative aspects in relation to any axis described herein. Proximal refers to a position closer to the exterior or the body or a user, whereas distal refers to a position closer to the interior of the body or further away from the user. Appending the initials "P" or "D" to an element number signifies a proximal or distal location or direction.

The term "elongated" as used herein refers to any object that is substantially longer in relation to its width, such as an object having a length that is at least two times longer than its width along its longitudinal axis. Some elongated objects, for example, are axially extending in a proximal or distal direction along an axis. Unless claimed, these terms are provided for convenience and not intended to limit this disclosure to a particular location, direction, or orientation.

As used herein, terms such as "comprises," "comprising," or like variations, are intended to cover a non-exclusive inclusion, such that any aspect that comprises a list of elements does not include only those elements or steps, but may include other elements or steps not expressly listed or inherent thereto. Unless stated otherwise, the term "exemplary" is used in the sense of "example" rather than "ideal." Conversely, the terms "consists of" and "consisting of" are intended to cover an exclusive inclusion, such that an aspect that consists of a list of elements includes only those elements. As used herein, terms such as "about," "substantially," "approximately," or like variations, may indicate a range of values within +/−5% of a stated value.

Numerous aspects are now described. Some aspects may comprise generating, with an imaging element, a video feed (e.g., from a wide angle view) of a muscle wall; establishing, with a processor, markers on the muscle wall in selected frames of the video feed; tracking, with the processor, relative movements between the markers (e.g., a in a real-time, frame-to-frame manner, while smooth scanning movements applied by the user); and identifying, with the processor, a location of a contraction of the muscle wall based on the relative movements. Additional aspects may include determining characteristics of the contraction based on the relative movements, determining characteristics of the muscle wall with a sensor, and/or determining a condition of the muscle wall based on a correlation between characteristics of the contraction and/or characteristics of the muscle wall. In some aspects, the muscle wall is a bladder wall.

Figure 1:
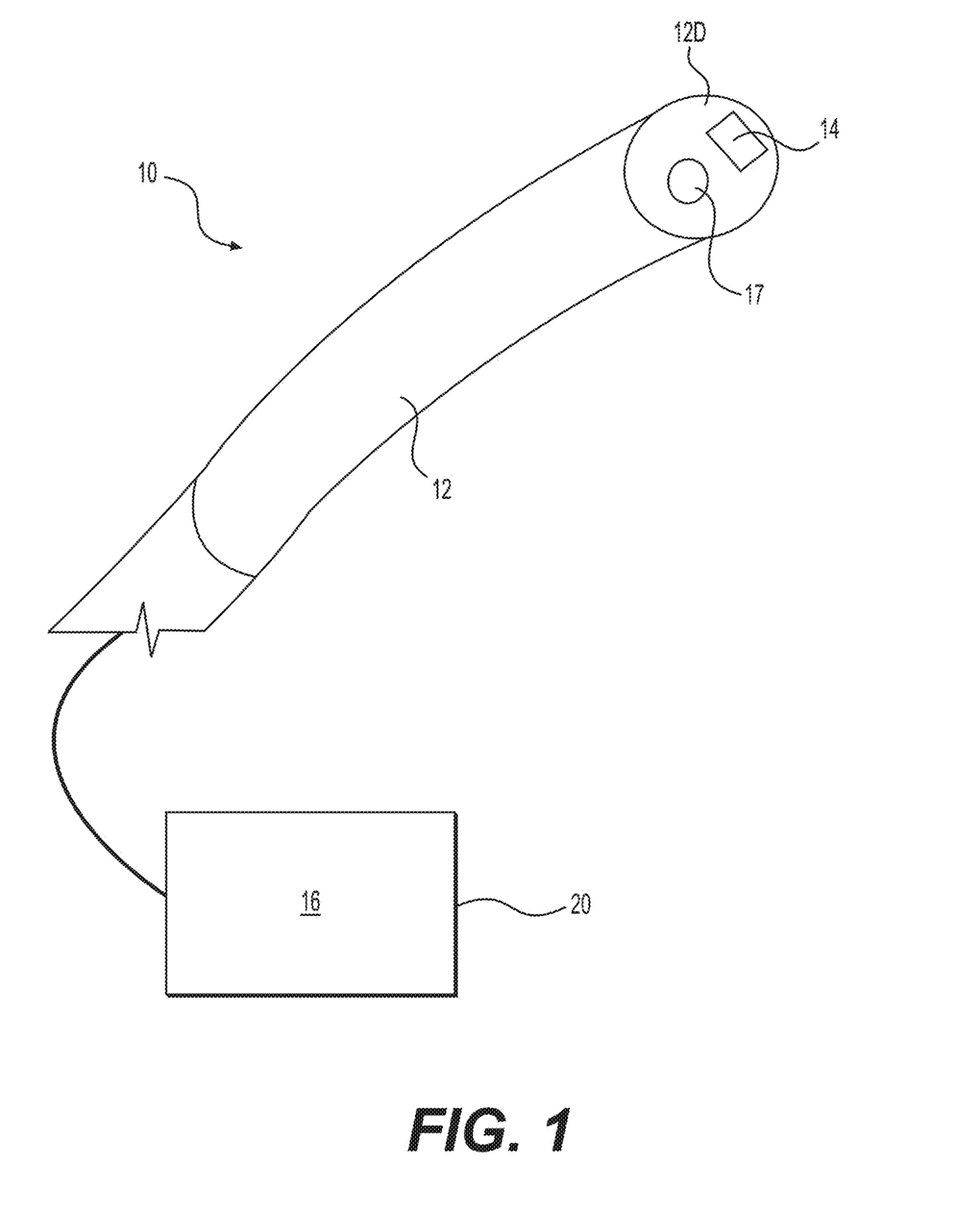
FIG. 1 depicts aspects of an exemplary imaging element.

Aspects of this disclosure are now described with reference to an exemplary scope 10 depicted in FIG. 1, and an exemplary method 100 depicted in FIG. 2. As shown in FIG. 1, scope 10 may comprise a shaft 12 with an imaging element 14 configured to capture a video feed 20; and a processor 16 configured to analyze the video feed 20 in real-time. Imaging element 14 may be a digital camera circuit located on a distal end 12D of shaft 12. Scope 10 of FIG. 1 may be, for example, a cystoscope, a ureteroscope, or like device with a lumen 17 extending longitudinally through shaft 12. Shaft 12 may be rigid or flexible. An exemplary scope 10 may include any of those sold by Boston Scientific Corporation, under the name Lithovue®. As shown in FIG. 3A, for example, scope 10 may be described with reference to a bladder or muscle wall 2 including a natural feature identifiable by imaging element 14, such as exemplary blood vessels 4. Any identifiable portion of wall 2 may be considered a natural feature. For example, any portion of blood vessels 4 may be considered a natural feature, including one or more bifurcations of vessels 4.

Figure 2:
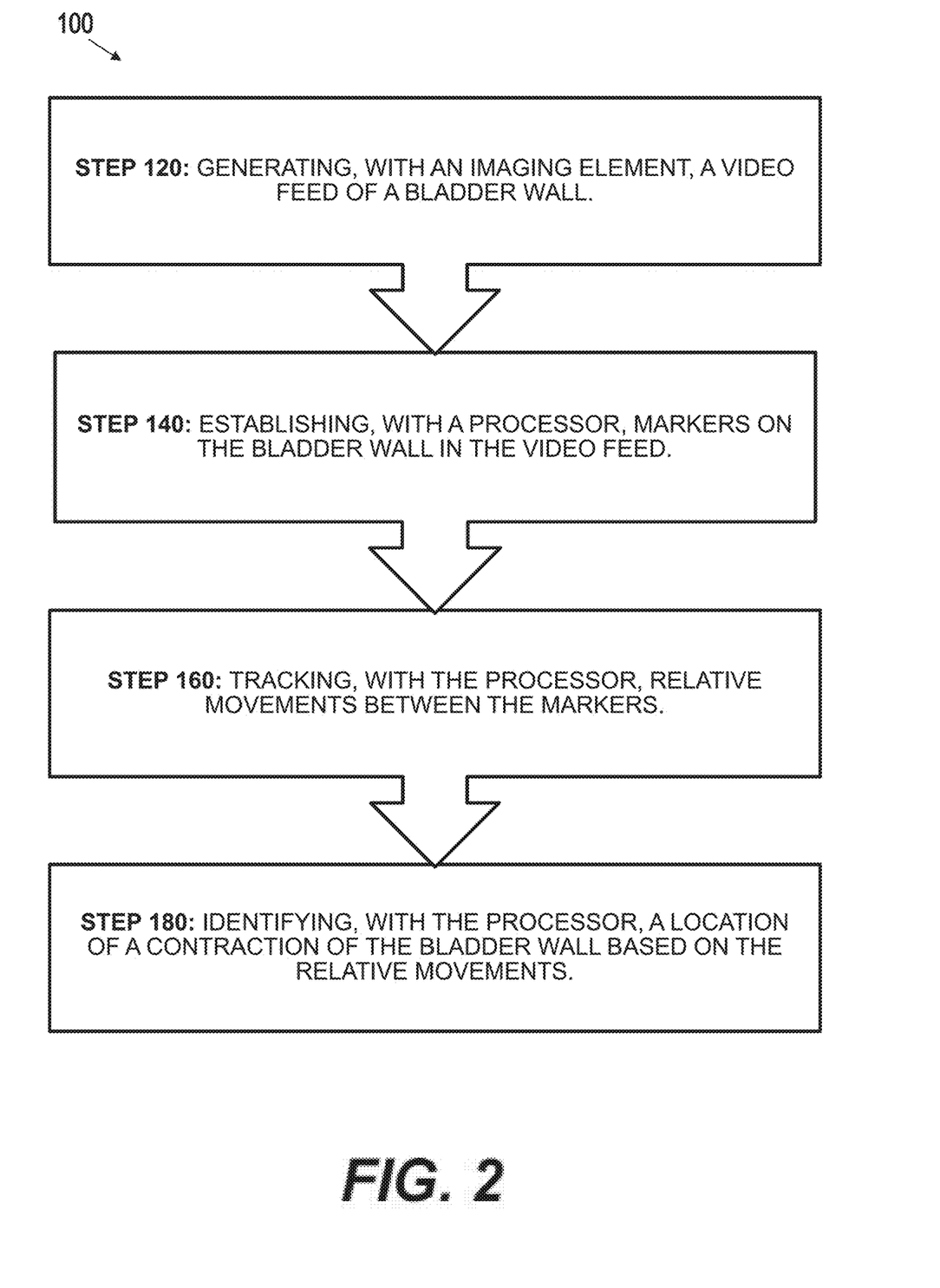
FIG. 2 depicts aspects of an exemplary method.
Figure 3A:
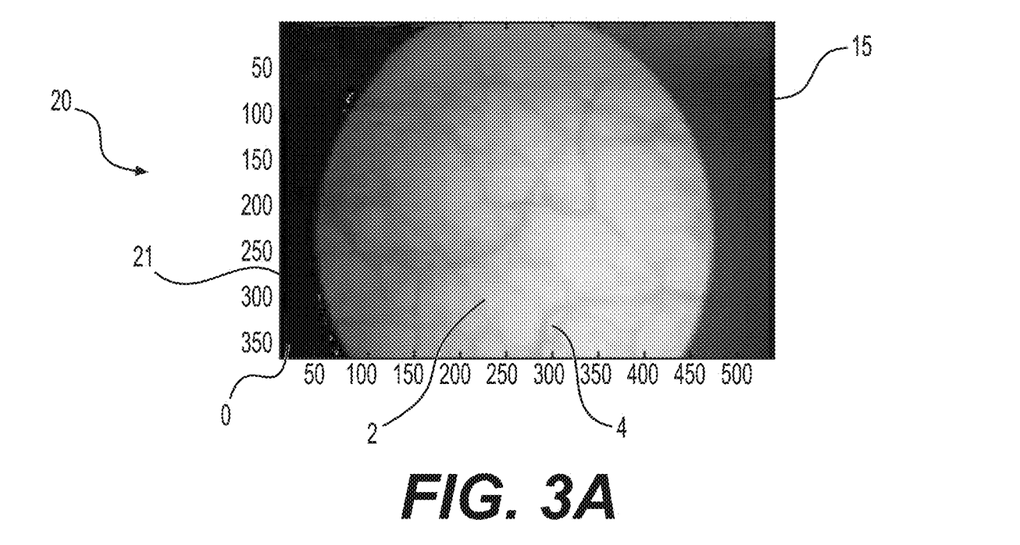
FIG. 3A depicts aspects of an exemplary frame of a video feed.

An exemplary method 100 is shown in FIG. 2. As shown, method 100 may comprise: generating, with imaging element 14, a video feed 20 of bladder wall 2 (a generating step 120); establishing, with processor 16, a plurality of markers 26 on bladder wall 2 in video feed 20 (an establishing step 140); tracking, with the processor 16, relative movements between the markers 26 (a tracking step 160); and identifying, with processor 16, a location of a contraction of bladder wall 2 based on the relative movements (an identifying step 180). Each step is now described in turn.

An exemplary frame 21 from video feed 20 is depicted in FIG. 3A. To generate frame 21, generating step 120 may comprise positioning scope 10 adjacent bladder wall 2, and activating imaging element 14 with processor 16. Imaging element 14 may be positioned adjacent to or mounted on either side of bladder wall 2. For example, as shown in FIG. 1, imaging element 14 may be mounted on distal end 12D of shaft 12 and either: guided subcutaneously through the body to a location adjacent an exterior surface of bladder wall 2; or guided through the urethra, bladder, and ureter to a location adjacent an interior surface of wall 2. Imaging element 14 may be operably coupled to processor 16 by a wired or wireless connection. Element 14 may mounted in or on distal end 12D, as in FIG. 1. Imaging element 14 also may be a stand-alone device. For example, element 14 may be an implantable medical device positioned to observe bladder wall 2; and generating step 120 may comprise affixing element 14 to an interior or exterior surface of bladder wall 2, and/or other surface in view of wall 2.

Generating step 120 may comprise any number of configuration steps. For example, step 120 may comprise selecting one or more frames 21 from video feed 20 (e.g., FIG. 3A), such as a first frame 21 and a second frame 21. Step 120 also may include defining an image area 15 of actual lens production for imaging element 14. Image area 15 may be determined once (e.g., by processor 16 and/or manual input) during the initial configuration of scope 10. As shown in FIG. 3A, image area 15 may be defined as a rectangular area with an origin point O at its bottom-left corner. Image area 15 may assume any shape. In FIG. 3A, area 15 includes a truncated circular area defined by a lumen of scope 10. Any shape may be included within area 15, such as non-circular and hexagonal shapes.

Generating step 120 may be configured to enhance the identifiability of natural features depicted in video feed 20. For example, step 120 may comprise applying a low pass filter to each frame 21; and/or selecting a color for each frame 21 that achieves high contrast between blood vessels 4 and bladder wall 2. Exemplary colors may be selected to produce gray level images of each frame 21. Generating step 120 may further comprise applying a median filter to each frame 21 to remove single pixel noise. Any additional or alternative graphical processing techniques may be used to enhance the identifiability of the depicted natural features within step 120.

Figure 4A:
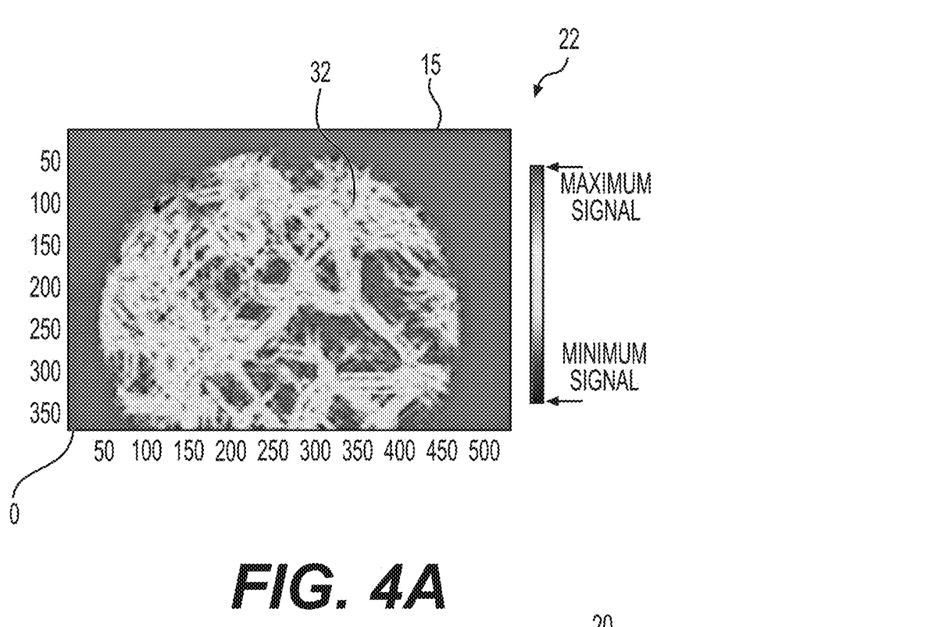
FIG. 4A depicts aspects of markers established with binary images.
Figure 4B:
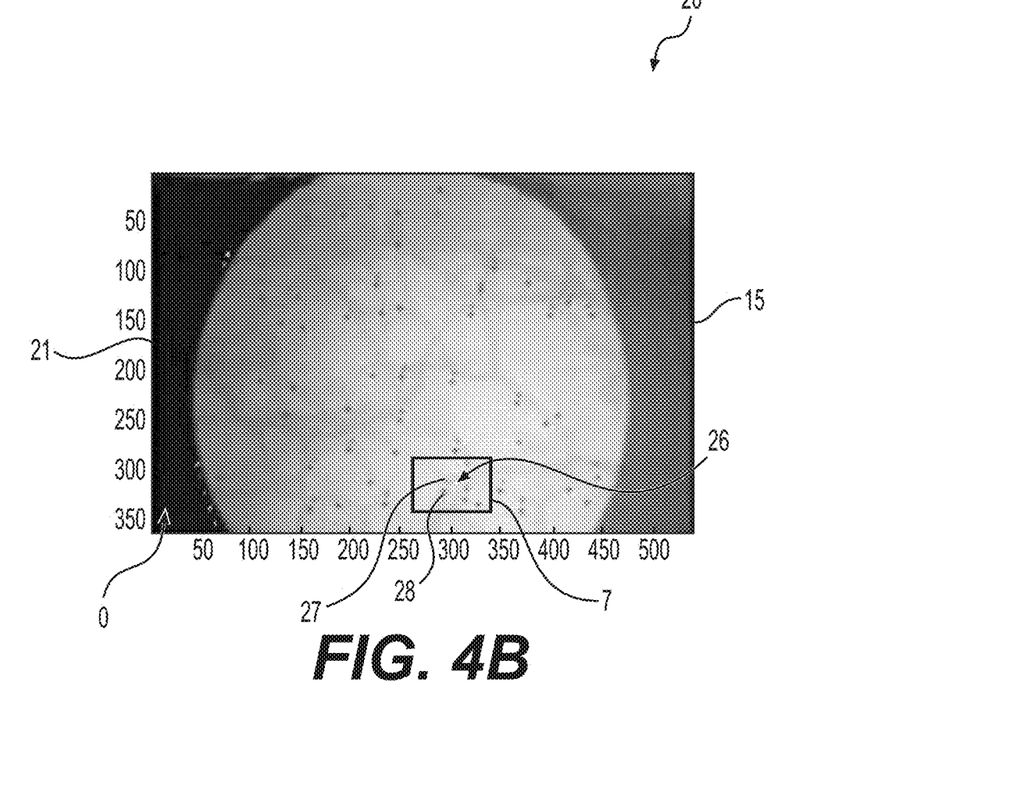
FIG. 4B depicts aspects of the frame of FIG. 3A overlaid with markers.

Establishing step 140 may comprise establishing, with processor 16, a plurality of markers 26 on bladder wall 2 in video feed 20. Each marker 26 may be assigned to a different portion of blood vessels 4. Step 140 may be repeated in successive frames 21 of video feed 20. For example, as shown in FIG. 4B, step 140 may comprise locating in a first frame 21 of video feed 20, with processor 16, a natural feature of the bladder wall 2 (e.g., a bifurcation of blood vessels 4); assigning, with processor 16, a first marker 27 to the natural feature in the first frame 21; locating in a second frame 21 of video feed 20, with processor 16, the same natural feature on bladder wall 2 (e.g., the same bifurcation of vessels 4); and assigning, with processor 16, a second marker 28 to the natural feature in the second frame 21.

Figure 3B:
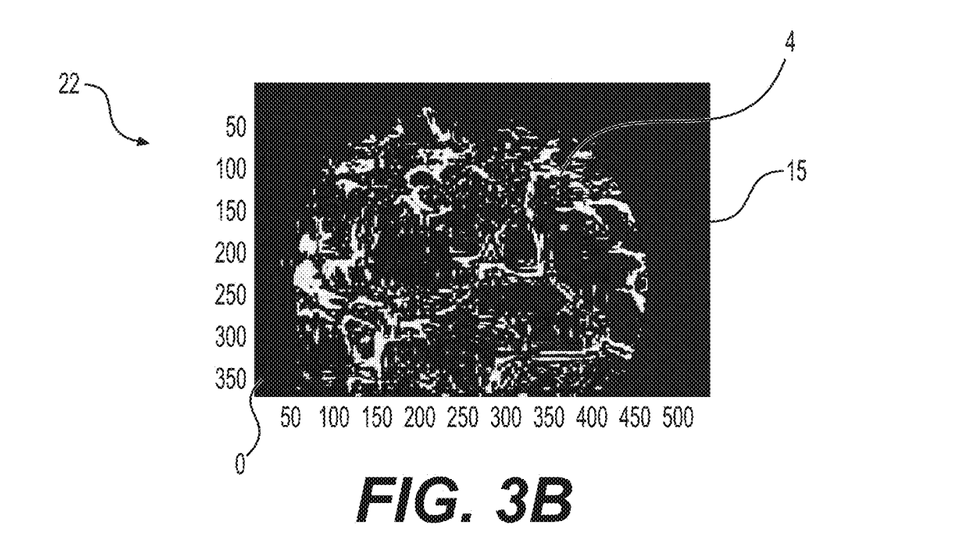
FIG. 3B depicts aspects of a binary image of the frame of FIG. 3A.

Within establishing step 140, the location of each marker 26 may be determined from a binary image 22 of each video frame 21. An exemplary binary image 22 is depicted in FIG. 3B. The location of each marker 26 may be defined in binary image 22 with reference to an X-Y coordinate plane centered at origin point O (shown in the bottom left corner in FIG. 3B, but may be located anywhere). Establishing step 140 may comprise: finding a threshold for detection of a natural feature of bladder wall 2 in each frame 21 (e.g., from an image histogram); creating a binary image 22 for each frame 21; and setting all pixels in the binary image above the threshold as "1", and those below the threshold as "0". As shown in FIG. 3B, the resulting binary image 22 may include data points defining a synthetic geometry of the blood vessels 4.

Aspects of this synthetic geometry may be utilized within establishing step 140. For example, the location of markers 26 (e.g., represented as $(X_i, Y_i)$) within each binary image 22 may be defined by searching data points from the synthetic geometry for correlation with the natural feature. Establishing step 140 may further comprise: generating, with processor 16, a correlation between a reference pattern and data points from the synthetic geometry. The locating step described above may comprise: locating in first and second binary images 22, with processor 16, the natural feature (e.g., the bifurcation of blood vessels 4) by generating a correlation between a reference pattern and data points selected from the synthetic geometry; and the assigning step described above may comprise assigning, with processor 16, first and second markers 27, 28 to the selected data points based on the correlation. Exemplary reference patterns may include any shape corresponding with the natural feature, including any "X" and/or "Y" shapes corresponding with one or more bifurcations of blood vessels 4.

To aid processor 16, establishing step 140 may comprise dividing each binary image 22 into segments (e.g., four segments) in order to spread markers 26 out evenly within image area 15. Processor 16 may include or be in communication with one or more sub-processors and/or memory components for this purpose. For example, establishing step 240 may comprise utilizing processor 16 to fill segments of each binary image 22 with an equal number of markers 26, allowing for parallel processing. In some aspects, each of the four segments may include n/4 markers 26, and each marker 26 may be assigned to a different portion of the natural feature.

Establishing step 140 may include iterative steps configured to determine and/or further refine the location of markers 26. As shown in FIG. 4A, for example, establishing step 140 may further comprise overlying a plurality of binary images 22 to enhance the synthetic geometry and/or define additional markers 26 based on local peaks 32. For example, a plurality of binary images 22 may be created by rotating imaging element 14 a fixed number of times when correlating the "X" shapes (e.g., four rotations), and orienting imaging element 14 a fixed number of times when correlating the "Y" shapes (e.g., one orientation). These steps may be repeated with modified magnification, for example, by reducing the original resolution by 2 for a total of 10 correlations. Additional markers 26 may be defined by overlaying the plurality of binary images 22, resulting in local peaks 32 (e.g., represented as Pk $(X_i, Y_i,$ value), each peak 32 including an X-Y position and a concentrated number (or value) of markers 26 located nearby. A graphical depiction of these iterative steps is depicted in FIG. 4A, wherein the local peaks 32 are shaded, by processor 16, according to a maximum or minimum number of markers 26 at each X-Y position.

Figure 10:
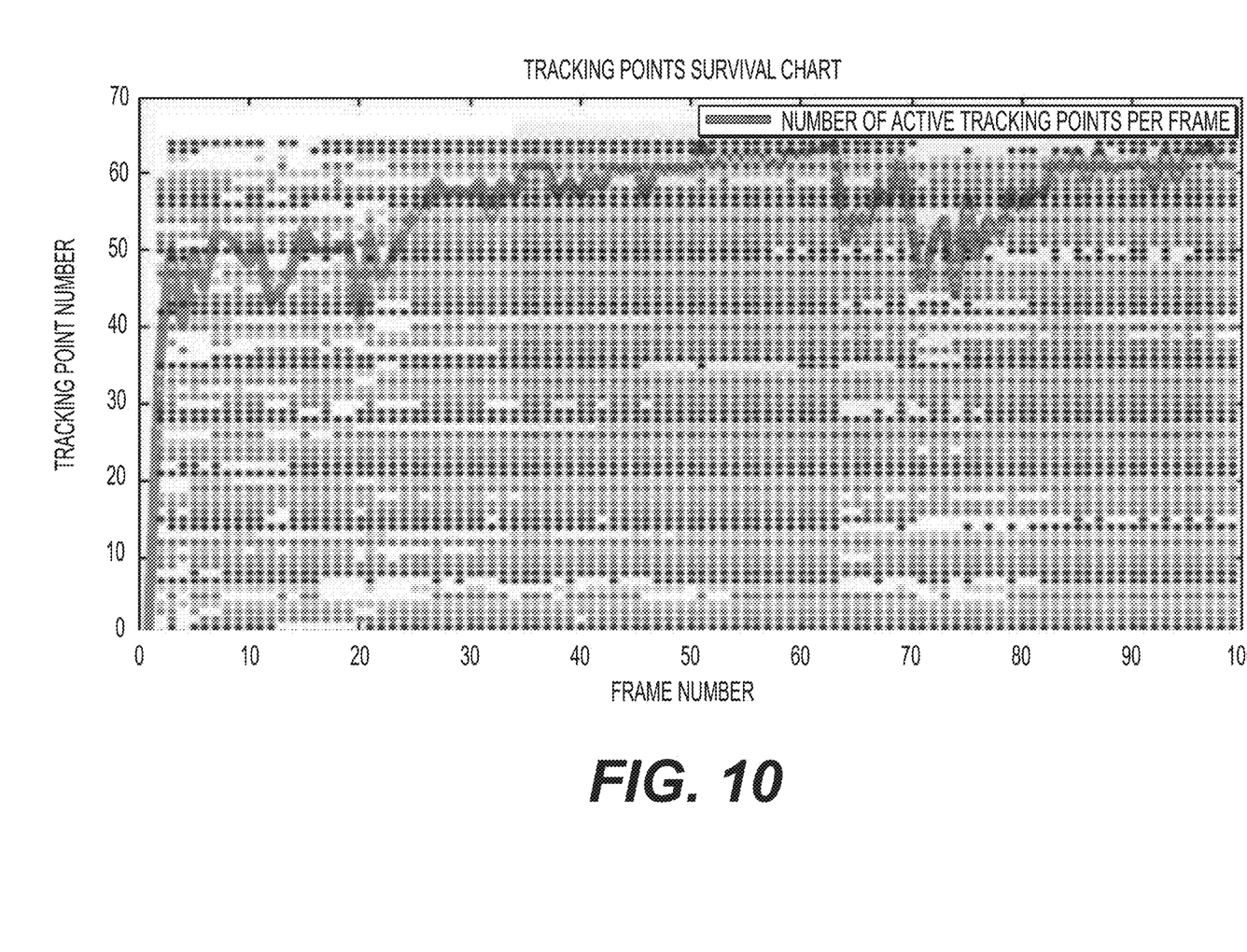
FIG. 10 depicts aspects of marker survival.

To simplify the data, and further aid processor 16, establishing step 140 may further comprise: sorting local peaks 32, and selecting the first n/4 values for further analysis. If the distance between any peaks 32 and/or markers 26 is too close, then step 140 may comprise eliminating one or more of the peaks 32 and/or markers 26. As indicated in FIG. 10, for example, some percentage of the markers 26 may not survive step 140 due to proximity with other markers 26. An exemplary survival chart is depicted in FIG. 10. As shown, for example, the average number of active markers 26 per frame may be 55, and the average lifetime of each marker 26 may be less than 10 frames. The average lifetime of each peak 32 may be similarly limited.

Tracking step 160 may comprise tracking, with processor 16, relative movements between markers 26. Aspects of tracking step 160 may be described with reference to FIG. 6B, which depicts first and second markers 27 and 28 together with a movement vector M extending therebetween. Relative movements between markers 27 and 28 may be quantified as a magnitude D of movement vector M. In some aspects, magnitude D may be displayed adjacent markers 27 and 28, as in FIG. 5.

Tracking step 160 may include correlating successive frames 21 and/or binary images 22 to determine an X-Y image move distance therebetween (e.g., represented by $(X_m, Y_m)$). To decrease processing time, tracking step 160 may comprise selecting a common portion of frames 21 and/or images 22 (e.g., a center portion of image area 15), and calculating the X-Y move distance with respect to the common portion. Similar to above, the resolution may be reduced in tracking step 160 (e.g., by ⅓ within the common portion) to further aid processor 16.

Tracking step 160 may further comprise establishing, with processor 16, a tracking area 7 that includes markers 26. Once tracking area 7 has been established, tracking step 160 may further comprise: analyzing, with processor 16, relative movements between markers 26 in tracking area 7 to determine one or more movement vectors M. Tracking area 7 may be located relative one or more peak values 32. For example, a size of tracking area 7 may be defined by a user during an initial configuration step (e.g., during or prior to generation step 120), and said size may be centered over a peak value 32 in tracking step 160.

Tracking step 160 may be configured to ensure that tracking area 7 is common to each frame 21 of video feed 20 by accounting for the X-Y image move between frames 21. For example, step 160 may comprise establishing a first tracking area 7 (e.g., represented by #i Pk $(X_i, Y_i)_{(t-1)}$) in a first frame 21. The size of said first tracking area 7 (e.g., represented by $(X_i, Y_i)_{(t-1)}$) may be defined by a user during an initial configuration step, and/or located relative to a peak value 32, as noted above. Tracking step 160 may further comprise establishing a second tracking area 7 (e.g., also represented by $(X_i, Y_i)_{(t-1)}$) in a second frame 21. To ensure commonality, second tracking area 7 may have the same size as the first tracking area 7, be located relative to the same peak value 32, and/or be shifted according to the X-Y image move (e.g., represented by $(X_i, Y_i)_{(t)} = (X_i, Y_i)_{(t-1)} + (X_m, Y_m)$).

Tracking step 160 also may include iterative steps configured to determine and further refine the location of markers 26. For example, the first and second tracking areas 7 may be correlated to find one or more second peak values (e.g., represented by $P_k (X_i, Y_i,$ value$)_{(t)}$), and/or establish additional markers 26. Other iterative steps may be performed based on the position and/or value of the second peak values. For example, if the position of the second peak value is too far from the correlated tracking area 7, or the value too low, then that peak value may be set to zero. Similar to above, step 160 may further comprise calculating a distance between each of the additional markers 26 and/or one or more second peak values, and eliminating any additional markers 26 and/or second peak values in close proximity to each other.

Identifying step 180 may comprise identifying, with processor 16, a location of a contraction of bladder wall 2 based on relative movements between markers 26. Identifying step 180 may be performed with processor 16, with or without graphical display (e.g., as in FIG. 4B). For example, step 180 may comprise: determining, with processor 16, a center of movement 6 (e.g., represented as $C_{(x,y)}$) for one or more movement vectors M in tracking area 7; a magnitude D of each movement vector M; and a distance $R_1$ from the center of movement 6 for each movement vector M. As now described, center of movement 6, magnitude D, and distance from center $R_1$ may be used within step 180 to identify the location of a contraction on bladder wall 2 and/or determine various characteristics of the contraction and wall 2.

Figure 6A:
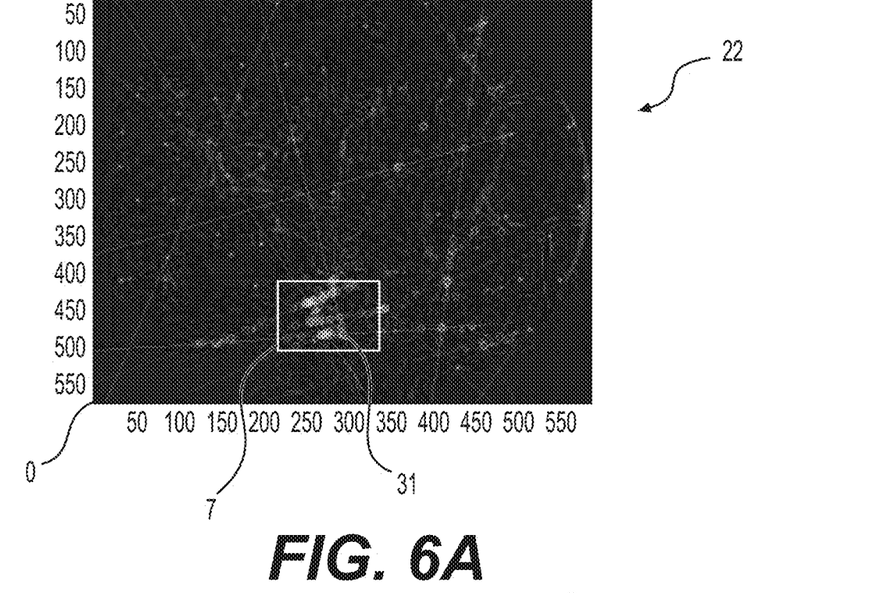
FIG. 6A depicts aspects of an exemplary tracking area.

As shown in FIG. 6A, for example, identification step 180 may comprise: projecting a longitudinal axis through each movement vector M in binary image 22; identifying points of intersection 31 (e.g., represented as X, Y) between the longitudinal axes; and defining center of movement 6 with respect to points of intersection 31. The proximity of these axes may be used to locate center of movement 6. For example, step 180 may comprise generating a movement array (e.g., represented by $d(X_i,Y_i)=(P_k(X_i,Y_i)_{(t)}-(P_k(X_i,Y_i)_{(t-1)}))$; calculating a relative movement array after compensating for the total image move (e.g., represented as $d(X_i,Y_i)_{(rel)}=P_k(X_i,Y_i)_{(t)}-(X_m,Y_m)*(-P_k(X_i,Y_i)_{(t-1)})$; transforming the relative movement array to a polar representation (e.g., represented as d(tta, D) in FIG. 7B); and determining coordinates for the center of movement 6 $(X_c, Y_c)$ from the average X and Y positions of all intersection points 31.

Figure 6B:
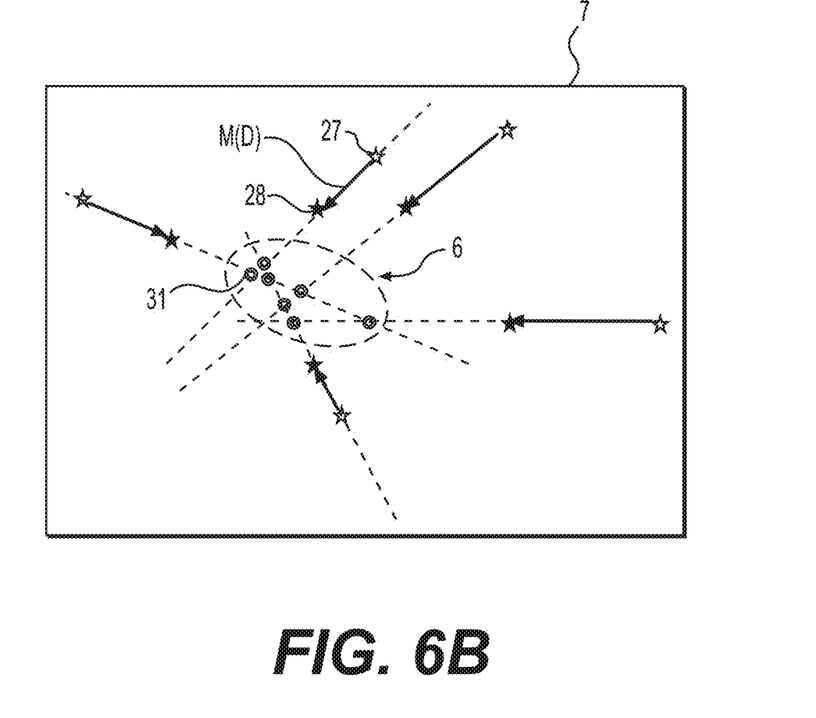
FIG. 6B depicts aspects of an exemplary center of movement.

Center of movement 6 may be defined by processor 16 within identification step 180. As shown in FIG. 6B, for example, each point of intersection 31 may be labeled with an indicator (e.g., shown in FIG. 6B as a circle), and the center of movement 6 may be defined as a circular area surrounding the points of intersection 31. Center of movement 6 may be used to analyze relative movements between markers 26. For example, identifying step 180 may further comprise: comparing, with processor 16, relative movements between markers 26 and center of movement 6 with known movement characteristics; and determining, with processor 16, whether the relative movements were caused by a contraction of bladder wall 2 or a movement of imaging element 14.

Figure 7A:
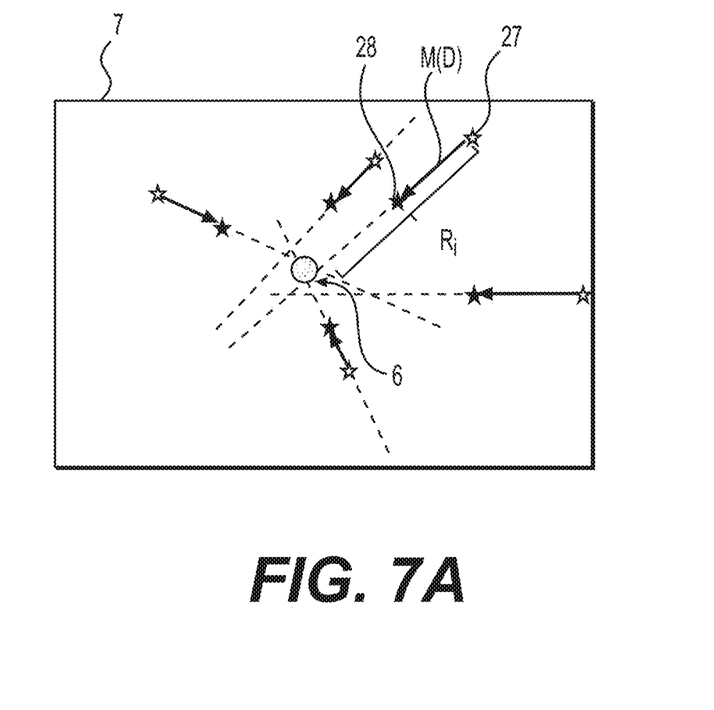
FIG. 7A depicts aspects of exemplary movement vectors.
Figure 7B:
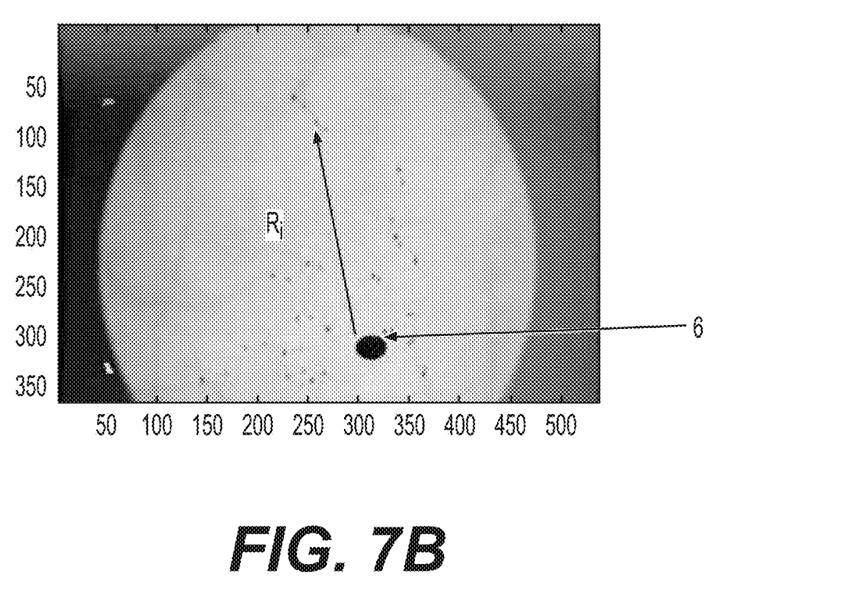
FIG. 7B depicts a polar representation of the vectors of FIG. 7A.

In step 180, magnitude M and distance from center $R_i$ may be compared with known movement characteristics to determine whether the relative movements were caused by a contraction of wall 2 and/or a movement of element 14. An example is depicted in FIG. 7A, wherein distance $R_i$ extends between first marker 27, second marker 28, and center of movement 6 along a longitudinal axis of vector M. Magnitude D may be used to determine whether the relative movements include a contraction. For example, identification step 180 may comprise qualifying, with processor 16, a movement of bladder wall 2 as a contraction if the distance $R_i$ is greater than approximately 3 pixels and appears in at least 2 consecutive binary images 22.

Figure 9A:
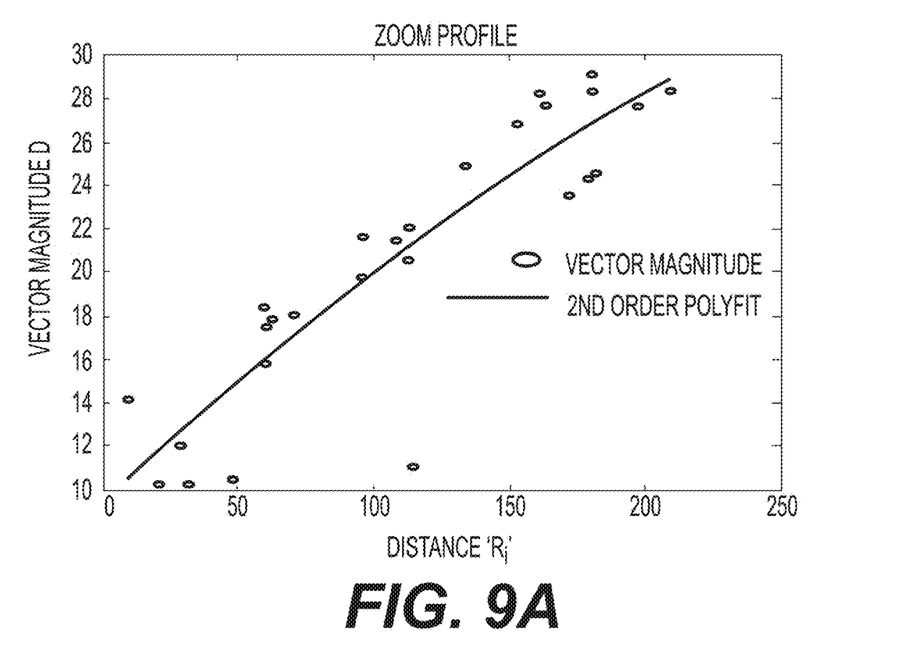
FIG. 9A depicts aspects of zoom characteristics.
Figure 9B:
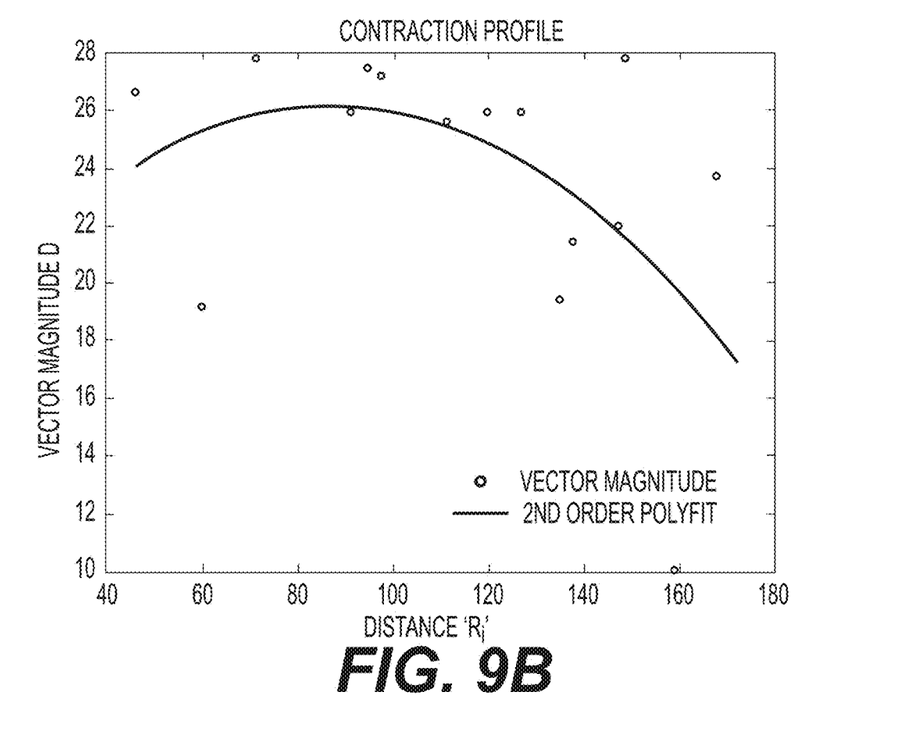
FIG. 9B depicts aspects of movement characteristics.

A relationship (e.g., a ratio) between magnitude D and distance $R_i$ also may be used to qualify the relative movements within identification step 180. For example, step 180 may comprise: generating, with processor 16, a ratio of magnitude D of each movement vector M to the distance $R_i$ from center of movement 6 for each vector M; qualifying, with processor 16, the contraction when the ratio is parabolic; and/or disqualifying, with processor 16, the contraction when the ratio is linear. Exemplary relationships between D and R are depicted in FIG. 9A, which depicts a linear relationship; and FIG. 9B, which depicts a non-linear or parabolic relationship. According to this disclosure, the linear relationship may be associated with a zooming movement of imaging element 14, whereas the non-linear relationship may be associated with a contraction of bladder wall 2.

Figure 8A:
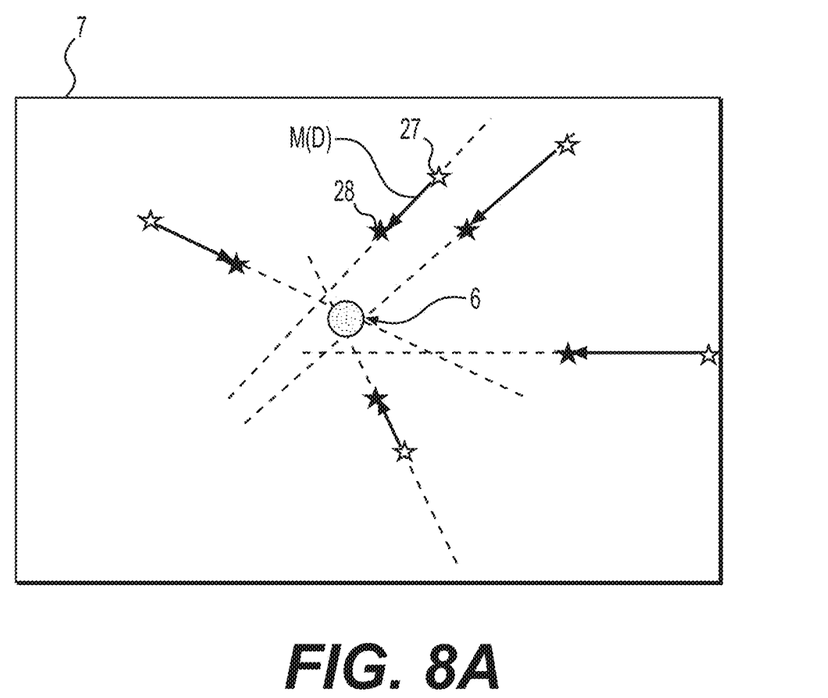
FIG. 8A depicts aspects of a zooming motion.
Figure 8B:
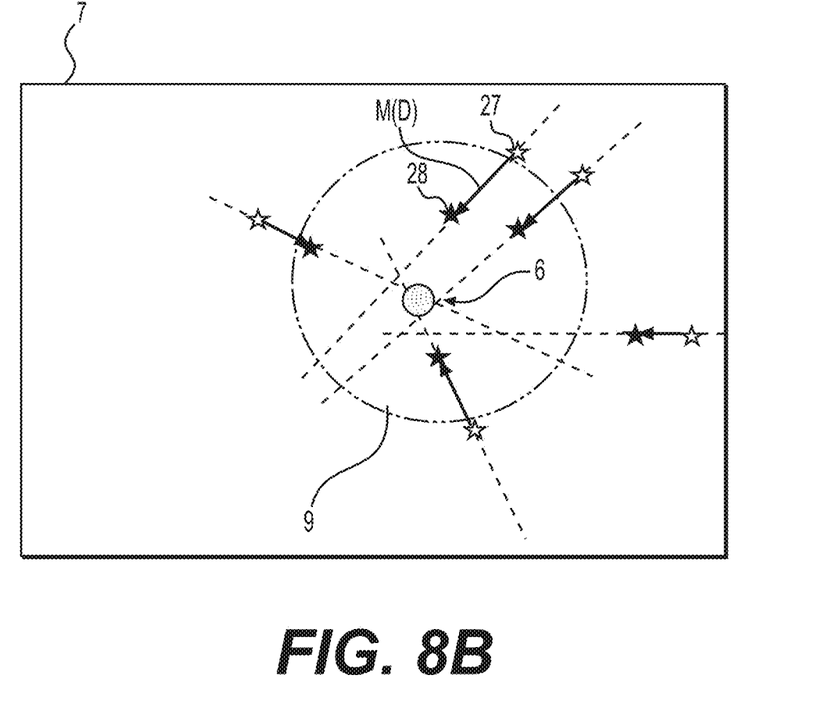
FIG. 8B depicts aspects of a contraction.

An exemplary zooming motion is depicted in FIG. 8A, wherein center of movement 6 is defined by points of intersection 31 (e.g., FIGS. 6A and 6B), or as an average of points 31, as described above. Magnitude D has a linear relationship with distance $R_i$ in FIG. 8A, meaning that a length of vector M will grow linearly with distance $R_i$ at all points within image area 15, indicating a zooming movement. An exemplary contraction is depicted in FIG. 8B, wherein magnitude D has a parabolic relationship with distance $R_i$. In FIG. 8B, for example, a length of movement vector M grows linearly with distance $R_i$ from center of movement 6 until the end of a contraction area 9 of image area 15, and then declines beyond contraction area 9, indicating a contraction.

Method 100 may comprise additional steps for determining characteristics of a contraction of bladder wall 2. For example, method 100 may further comprise determining from the relative movements, with processor 16, characteristics of the contraction including at least one of a contraction strength, a contraction frequency, a contraction profile, a contraction duration, and a contraction density. In some aspects, method 100 may further comprise: diagnosing, with processor 16, a condition of bladder 2 wall based on the characteristics of the contraction. Conditions such as overactive or atonic bladder, for example, may be diagnosed with processor 16 based on one or more of these characteristics. If bladder wall 2 is a muscle wall not associated with the bladder, then conditions of the muscle wall may be similarly diagnosed.

Method 100 also may comprise additional steps for determining characteristics of bladder wall 2. For example, method 100 may comprise: monitoring, with a sensor, characteristics of bladder wall 2 including at least one of a fluid pressure applied to wall 2 and a volume of fluid retained by the wall 2; and generating, with processor 16, a correlation between characteristics of the contraction and characteristics of the bladder wall 2. Method 100 may further comprise diagnosing, with processor 16, the condition of wall 2 based on at least one of the characteristics of the contraction, the characteristics of bladder wall 2, and the correlation therebetween. The sensor may be mounted on shaft 12, integral with imaging element 14, or a stand-alone element. In some aspects, for example, contraction strength may be correlated with fluid pressure to further distinguish overactive bladder from other conditions. Similar correlations may be made to diagnose conditions of other muscle walls.

Once contractions of bladder wall 2 have been located and/or qualified, method 100 may further comprise: selecting, with processor 16, locations of bladder wall 2 for a treatment; determining, with processor 16, characteristics of the treatment; and/or applying the treatment to the selected locations. For example, locations of bladder wall 2 may be selected based upon characteristics of the contraction, such as contraction strength; or characteristics of the bladder wall, such as fluid pressure. The treatment may include a wave energy (e.g., laser, sound, etc.), and characteristics of the treatment may include intensity, power level, duration, pulsing, and the like. If the wave energy is a laser energy, then method 100 may comprise: delivering the laser energy to the location of each contraction, for example, by passing an optical fiber through lumen 17, and delivering the laser energy through the optical fiber.

Figure 5:
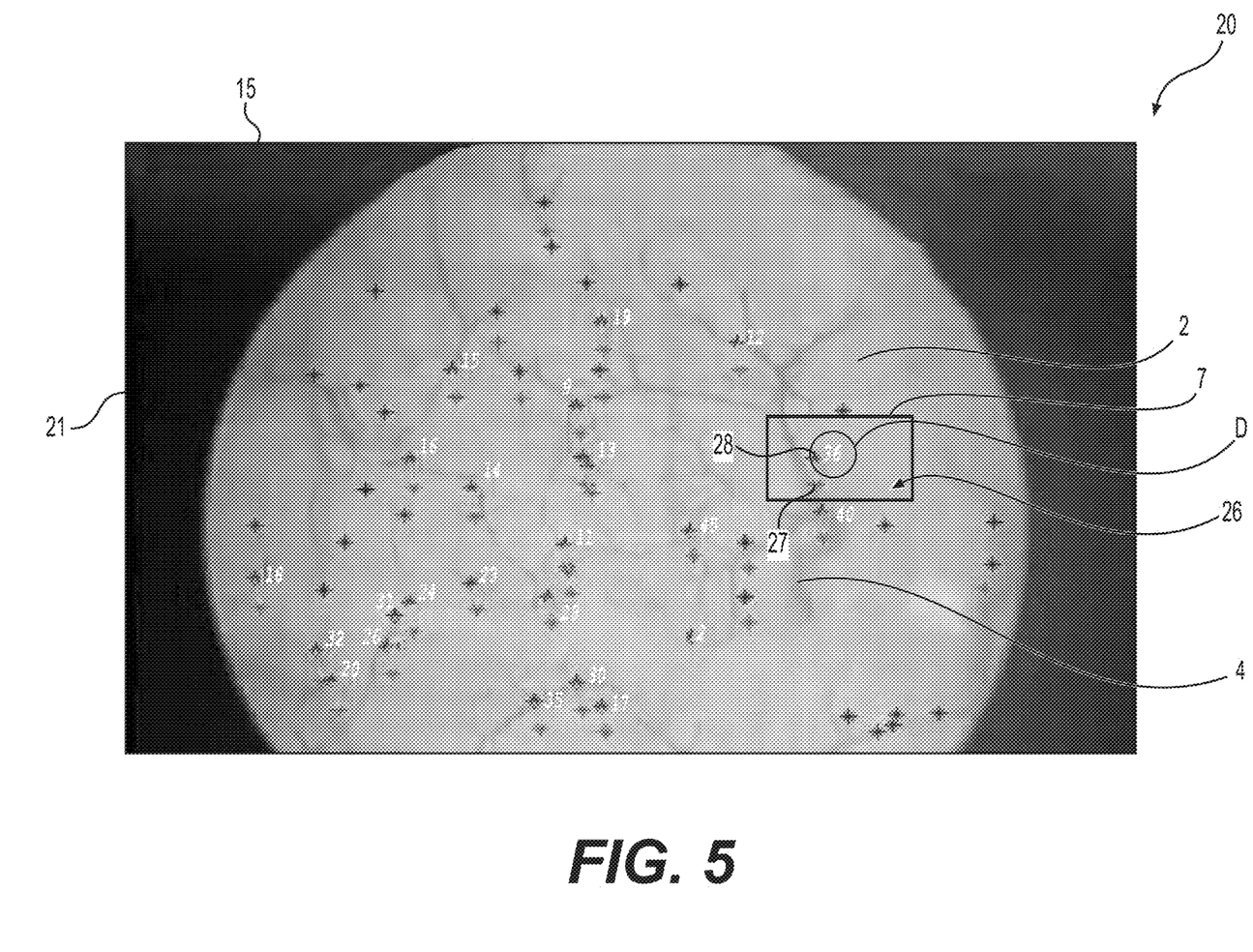
FIG. 5 depicts additional aspects the frame and markers of FIG. 4B.

Any step of method 100 may further comprise: outputting, with processor 16, video feed 20 to a display device (e.g., a two- or three-dimensional monitor); and/or overlaying, with processor 16, indicators onto frames 21. Exemplary indicators may be provided at the location of each contraction. As shown in FIG. 5, indicators also may be provided for each marker 26, each vector M extending therethrough, and each magnitude D associated therewith. Other indicators may be provided for any of the contraction and/or bladder wall characteristics described herein. In some aspects, method 100 further comprises overlaying, with processor 16, these indicators in real-time for continuous monitoring of bladder wall 2.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

The invention claimed is:

1. A method comprising:
generating, with an imaging element, a video feed depicting a bladder wall;
establishing, with a processor, virtual markers on the bladder wall in the video feed;
tracking, with the processor, relative movements between the virtual markers in real-time, by the processor analyzing the video-feed in real-time, wherein real-time is when each of the relative movements occur in the video feed; and
identifying, with the processor, a location of a contraction of the bladder wall based on the relative movements.

2. The method of claim 1, wherein generating the video feed comprises positioning the imaging element adjacent an interior surface of the bladder wall.

3. The method of claim 1, wherein establishing the virtual markers comprises:
locating in a first frame of the video feed, with the processor, a natural feature of the bladder wall;
assigning, with the processor, a first virtual marker to the natural feature in the first frame;
locating in a second frame of the video feed, with the processor, the natural feature on the bladder wall; and
assigning, with the processor, a second virtual marker to the natural feature in the second frame.

4. The method of claim 1, wherein:
establishing the virtual markers further comprises generating, with the processor, a first binary image of the first frame and a second binary image of the second frame;
each of the first and second binary images include data points defining a synthetic geometry of the natural feature; and
the locating and assigning steps further comprise:
locating in the first and second binary images, with the processor, the location of the natural feature by generating a correlation between a reference pattern and data points from the synthetic geometry; and
assigning, with the processor, the first and second virtual markers to the data points based on the correlation.

5. The method of claim 4, wherein the reference pattern includes a X or Y shape corresponding with a blood vessel bifurcation.

6. The method of claim 1, wherein:
tracking the relative movements comprises:
establishing, with the processor, a tracking area of the bladder wall in the first and second frames that includes the first and second virtual markers; and
analyzing, with the processor, relative movements between the first and second virtual markers in the tracking area to determine one or more movement vectors; and
identifying the location of the contraction comprises analyzing the one or more movement vectors.

7. The method of claim 6, wherein identifying the location of the contraction comprises:
locating, with the processor, a center of movement for the one or more movement vectors in the tracking area; and
determining, with the processor, a magnitude of each movement vector and a distance from the center of movement for each movement vector.

8. The method of claim 7, further comprising:
comparing, with the processor, the magnitude and distance of each movement vector with known movement characteristics to determine whether the relative movements were caused by the contraction or a movement of the imaging element.

9. The method of claim 8, further comprising:
generating, with the processor, a ratio of the magnitude of each movement vector to the distance from the center of movement for each movement vector;
qualifying, with the processor, the contraction when the ratio is parabolic; and
disqualifying, with the processor, the contraction when the ratio is linear.

10. The method of claim 1, further comprising:
determining from the relative movements, with the processor, characteristics of the contraction including at least one of a contraction strength, a contraction frequency, a contraction profile, a contraction duration, and a contraction density; and
diagnosing, with the processor, a condition of the bladder wall based on the characteristics of the contraction.

11. The method of claim 8, further comprising:
monitoring, with a sensor, characteristics of the bladder wall including at least one of a fluid pressure applied to the bladder wall and a volume of fluid retained by the bladder wall;
generating, with the processor, a correlation between the characteristics of the contraction and the characteristics of the bladder wall; and
diagnosing, with the processor, the condition of the bladder wall based on at least one of the characteristics of the contraction, the characteristics of the bladder, and the correlation therebetween.

12. A method comprising:
locating in frames of a video feed, with a processor, a natural feature of a bladder wall depicted in the video feed;
assigning, with the processor, virtual markers to the natural feature in each frame of the video feed;
establishing, with the processor, a tracking area of the bladder wall in video feed that includes first and second virtual markers;
analyzing, with the processor, relative movements of the virtual markers in the tracking area to determine one or more movement vectors in real-time, by the processor analyzing the video-feed in real-time, wherein real-time is when each of the relative movements occur in the video feed;

locating, with the processor, a center of movement for the one or more movement vectors; and qualifying, with the processor, a movement of the bladder wall as a contraction based a ratio between the magnitude of each movement vector and a distance from the center of movement for each movement vector, wherein assigning the virtual markers comprises:

locating in a first frame of the video feed, with the processor, a natural feature of the bladder wall;

assigning, with the processor, the first virtual marker to the natural feature in the first frame;

locating in a second frame of the video feed, with the processor, the natural feature on the bladder wall; and assigning, with the processor, the second virtual marker to the natural feature in the second frame.

13. The method of claim 12, wherein the natural feature includes a blood vessel bifurcation.

14. The method of claim 12, further comprising:

generating, with the processor, a binary image of each frame in the video feed, each binary image including data points defining a synthetic geometry of the bladder wall;

locating in each binary image, with the processor, the natural feature by generating a correlation between a reference pattern and data points from the synthetic geometry; and assigning, with the processor, the first and second virtual markers to the data points based on the correlation.

15. The method of claim 12, further comprising:

identifying, with the processor, the location of each qualified contraction based on the one or more movement vectors;

outputting, with the processor, the video feed to a display device; and overlaying onto the video feed, with the processor, the location of each qualified contraction, and characteristics of each qualified contraction including at least one of a contraction strength, a contraction frequency, a contraction profile, a contraction duration, and a contraction density.

16. The method of claim 15, further comprising:

monitoring, with one or more sensors, characteristics of the bladder wall including at least one of a fluid pressure applied to the bladder wall and a fluid volume retained by the bladder wall;

generating, with the processor, a correlation between the characteristics of each qualified contraction and the characteristics of the bladder wall; and diagnosing, with the processor, the condition of the bladder wall based on at least one of the characteristics of the contraction, the characteristics of the bladder wall, and the correlation therebetween.

17. A method comprising:

selecting from a video feed, with a processor, a first frame depicting a bladder wall, and a second frame depicting the bladder wall;

generating, with the processor, a first binary image of the first frame and a second binary image of the second frame;

locating in the first and second binary images, with the processor, one or more blood vessel bifurcations of the bladder wall;

assigning, with the processor, a first virtual marker relative to the one or more blood vessel bifurcations in the first frame, and a second virtual marker relative to the one or more blood vessel bifurcations in the second frame;

calculating, with the processor, relative movements between the first and second virtual markers in real-time, by the processor analyzing the video-feed in real-time, wherein real-time is when each of the relative movements occur in the video feed; and identifying, with the processor, a location of one or more contractions of the bladder wall based on the relative movements.

18. The method of claim 17, further comprising receiving the video feed, at the processor, from an imaging element positioned adjacent the bladder wall.

19. The method of claim 18, further comprising:

determining from the relative movements, with the processor, characteristics of the contraction;

monitoring, with a sensor, characteristics of the bladder wall including at least one of a fluid pressure applied to the bladder wall and a volume of fluid retained by the bladder wall; and generating, with the processor, a correlation between the characteristics of the contraction and the characteristics of the bladder wall.

20. The method of claim 19, further comprising diagnosing, with the processor, a condition of the bladder wall based on at least one of the characteristics of the contraction, the characteristics of the bladder wall, and the correlation therebetween.

* * * * *